United States Patent [19]

Wang

[11] 4,424,220

[45] Jan. 3, 1984

[54] TREATMENT OF GIARDIASIS AND TRICHOMONIASIS

[75] Inventor: Ching C. Wang, San Francisco, Calif.

[73] Assignee: Merck & Co., Inc., Rahway, N.J.

[21] Appl. No.: 421,595

[22] Filed: Sep. 22, 1982

Related U.S. Application Data

[62] Division of Ser. No. 347,655, Feb. 10, 1982.

[51] Int. Cl.$^3$ .......................................... A61K 31/495
[52] U.S. Cl. ................................................... 424/250
[58] Field of Search ........................................ 424/250

[56] References Cited

PUBLICATIONS

Chemical Abstracts 71: 110119u (1969).

*Primary Examiner*—Jerome D. Goldberg
*Attorney, Agent, or Firm*—David L. Rose; William H. Nicholson; Mario A. Monaco

[57] ABSTRACT

Fluorouracil and emimycin are useful in the treatment of giardiasis and trichomoniasis.

1 Claim, No Drawings

TREATMENT OF GIARDIASIS AND TRICHOMONIASIS

CROSS REFERENCE TO RELATED APPLICATIONS

This application is a divisional application of my co-pending application Ser. No. 347,655 filed Feb. 10, 1982.

BACKGROUND OF THE INVENTION

Giardia lamblia, a parasite that until recently was widely believed to be relatively harmless, now heads the list of the most common intestinal parasitic infections in the United States and some other countries. The parasite causes a diarrheal disease call giardiasis.

This infection causes a variety of intestinal symptoms, such as prolonged diarrhea, abdominal cramps, stomach pain, severe weight loss, fatigue, nausea and flatulence. Giardiasis can also cause malabsorption of nutrients and even retarded growth. Furthermore, giardiasis can mimic the symptoms of other conditions such as ulcers and gall bladder attacks. If misdiagnosed, a patient may have a series of costly, needless tests, and even surgery.

The infection can be successfully treated with one of three drugs: Atabrine, Flagyl or furazolidone. However, each of these drugs is known to cause adverse side effects. Until the present invention no prophylactic drug has been found which can adequately protect against giardiasis. (L. K. Altman, M.D., The New York Times, June 10, 1980).

Trichomoniasis is an infection of the lower genito-urinary tract, which may be induced in men and women by the protozoan parasite Trichomonas vaginalis. The infection may produce a few symptoms of such extreme discomfort and morbidity that intervention from a gynecologist or a urologist is necessary. The disease is of cosmopolitan distribution and apparently 10–25% of sexually mature females and 25–80% of their consorts are involved (E. A. Steck, The Chemotherapy of Protozoan Diseases, Vol. II, Section 3, 17-1 (1971). Trichomoniasis is presently treated with Flagyl(metronidazole). The present invention relates to the use of 5-fluoro-2,4-(1H,3H) pyrimidenedione (fluorouracil) or 2-hydroxypyrazine-4-oxide(emimycin) in the treatment of giardiasis and trichomoniasis in humans.

SUMMARY OF THE INVENTION

The present invention is directed to the novel method for control and treatment of giardiasis, a parasitic infection in humans caused by protozoa of the genus Giardia.

The novel compositions used in the present method can also be used for the prevention, treatment and control of trichomoniasis in men and women.

Therefore, it is an object of the present invention to (1) provide novel pharmaceutical composition comprising fluorouracil or emimycin with anti-giardiasis and anti-trichomoniasis activities; (2) provide a novel method for the prevention, control and/or treatment of giardiasis and trichomoniasis in humans through the administration of the novel compositions.

DETAILED DESCRIPTION OF THE INVENTION

The compounds useful in the novel methods of treatment of this invention have the following structural formulae:

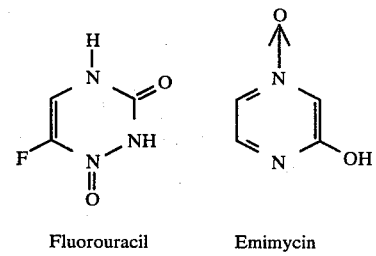

Fluorouracil    Emimycin

The activity of these compounds against Giardia lamblia and Trichomonas foetus are shown by the following test:

About 1.0–2.0 ml of a nutrient medium, for example, the modified Diamond's TPS medium at pH 7.05, together with about 10% by volume of heat-inactiviated serum and about 1% by volume of antibiotic-antimycotic solution is placed in each well of a multiwell plate. To this mixture, an aliquot of a suspension of G. lamblia cells containing about $10^6$ organisms is added. Subsequently, each well is inoculated with a known concentration of one of the active compounds. The multiwell plate containing the individual culture samples is incubated under anaerobic conditions at about 37° C. for about 16–24 hrs. The number of viable cells remaining in each well are then counted, such as with a hemacytometer. The percentage of survival is determined by comparison with controls inoculated with DMSO (dimethylsulfoxide) and the effective concentration (in parts per million) for 50% inhibition of growth ($ED_{50}$) is determined. It is established that the lower the number of the value of $ED_{50}$, the higher the activity of the active compound. The $ED_{50}$ values of the active compounds are summarized below in Table I.

TABLE 1

| In vitro Anti-G. lamblia and anti-T. foetus activities of fluoruracil and emimycin | | |
|---|---|---|
| Compound | Anti-G. lamblia $ED_{50}$ (ppm) | Anti-T. foetus $ED_{50}$ (ppm) |
| (1) fluorouracil | 100 | 3 |
| (2) emimycin | 22.0 | <1.0 |

The novel method of this invention comprises the administration of fluorouracil or emimycin as an anti-giardiasis or anti-trichomoniasis agent to a human patient in amounts ranging from about 0.05 to about 50 mg. per kg. of body weight, preferably from about 0.25 to about 25 mg. per kg. of body weight in a single dose or in 2 to 4 divided doses.

These compounds in the described dosages are usually administered orally. They may also be administered to individuals by injection. The oral phamaceutical compositions of this invention usually consist of an active compound and some appropriate excipients and used in the form of tablets, troches, capsules, elixirs, suspensions, syrups, wafers, chewing gum and the like. The amount of an acitive compound in such a therapeutically useful composition or preparation usually ranges from about 2.5 mg. to about 2.5 g. preferably from about 5 mg. to about 500 mg. per unit dosage.

The previously described tablets, troches, capsules, pills and the like usually contain one or more of the following inactive ingredients: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin and/or a flavoring agent such as peppermint, oil of wintergreen, or cherry flavoring. When the dosage unit form is a capsule, it may contain in addition to materials of the above type, a liquid carrier such as fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

EXAMPLE 1

In each well of a multiwell plate is placed 1.4 ml of media mix containing Diamond's TPS medium (see Table 2) at pH 7.05, 10% by volume of heat-inactivated fetal bovine serum, and 1% by volume of an antibiotic-antimycotic solution (see Table 3). A suspension of *Giardia lamblia* is centrifuged at 2,500 xg. for 6 minutes. The cells are resuspended in a small volume of the Diamond's medium, counted, and each well inoculated with approximately $10^6$ organisms. A stock solution of fluorouracil is made at a concentration of 150 μg/ml. The wells are then inoculated with various concentrations of the drug. The plates are incubated for 24 hours at 37° C. in an anaerobic Gas Pak jar. After 24 hours of incubation each well is mixed and counted for viable organisms using a hemacytometer. The percentage of survival is determined by comparing the treated wells to controls treated with dimethylsulfoxide. The in vitro anti-*G. lamblia* activity of fluorouracil is determined in terms of $ED_{50}$ (effective dosage for 50% inhibition of growth) and has a $ED_{50}$ value of 100 ppm.

TABLE 2

| Composition of Diamond's TPS Medium | |
|---|---|
| Ingredients | Amounts |
| Trypticase (BBL) | 1.00 g |
| Panmede, liver digest P & B | 2.00 g |
| Glucose | 0.50 g |
| L-cysteine monohydrochloride | 0.10 g |
| Ascorbic acid | 0.02 g |
| Sodium chloride | 0.05 g |
| Potassium phosphate-monobasic | 0.06 g |
| Potassium phosphate, dibasic anhydrous | 0.10 g |
| Water, glass distilled pH adjusted to 7.0 with 1 N NaOH | 87.50 ml |

TABLE 3

| Composition of antibiotic-antimycotic solution (100X) | |
|---|---|
| Penicillin, | 10,000 units |
| Streptomycin | 10,000 mcg. |
| Fungizone ® | 25 mcg. |
| Prepared in 1 ml. of normal saline. | |

Employing substantially the similar procedure as described in Example 1 but substituting for fluorouracil used therein the other active compound emimycin, there is obtained similar results indicating the anti-*G. lamblia activities of the compounds included above in Table 1*.

Similarly, following essentially the same procedure described above, the hydrochloride salts of the compounds are found to be equally active as the corresponding free base.

EXAMPLE 2

Employing essentially the same method of Example 1, centrifuged cells of *T. foetus* $KV_1$ are inoculated with fluorouracil at 37° C. for 24 hours. The results indicate that this compound is also an effective anti-*T. foetus* agent with an $ED_{50}$ value of 3 ppm.

Similarly, emimycin and the pharmaceutically acceptable salts thereof are active anti-*T. vaginalis* agents as shown in Table 1.

EXAMPLE 3

| Preparation of Capsule Formulation | |
|---|---|
| Ingredient | Milligrams per Capsule |
| Fluorouracil | 10 |
| Starch | 100 |
| Magnesium Stearate | 10 |

The active ingredient, starch and magnesium stearate are blended together. The mixture is used to fill hard shell gelatine capsules of a suitable size at a fill weight of 120 mg per capsule.

EXAMPLE 4

| Preparation of Tablet Formulation | |
|---|---|
| Ingredient | Milligrams per Capsule |
| Emimycin | 12 |
| Lactose | 200 |
| Corn starch (for mix) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of the active ingredient.

What is claimed is:

1. A method of treating giardiasis and trichomoniasis in a human which comprises the administration to a human in need of said treatment of an effective antigiardiasis and antitrichomoniasis amount of 2-hydroxypyrazine-4-oxide.

* * * * *